(12) United States Patent
Ikhlef et al.

(10) Patent No.: US 8,926,177 B2
(45) Date of Patent: Jan. 6, 2015

(54) SOURCE SIDE MONITORING DEVICE FOR AN IMAGING SYSTEM

(75) Inventors: Abdelaziz Ikhlef, Hartland, WI (US); Joseph James Lacey, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 326 days.

(21) Appl. No.: 13/476,130

(22) Filed: May 21, 2012

(65) Prior Publication Data
US 2013/0308748 A1    Nov. 21, 2013

(51) Int. Cl.
*G01D 18/00*    (2006.01)

(52) U.S. Cl.
USPC .......................................... 378/207

(58) Field of Classification Search
CPC ..... G01N 23/04; G01N 23/06; G01N 23/083; A61B 6/58; A61B 6/582; A61B 6/585; A61B 6/586; H05G 1/26; H05G 1/265

USPC .................. 378/4, 19, 62, 162, 165, 204, 207
See application file for complete search history.

(56) References Cited

U.S. PATENT DOCUMENTS 5,550,886 A * 8/1996 Dobbs et al. .................... 378/19
6,996,206 B2   2/2006 Hsieh et al.

OTHER PUBLICATIONS

U.S. Appl. No. 13/163,367, filed Jun. 17, 2011, Methods and apparatus for collimation of detectors.
U.S. Appl. No. 13/166,987, filed Jun. 23, 2011, Systems and Methods for Focal Spot Motion Correction.

* cited by examiner

*Primary Examiner* — Jurie Yun

(57) ABSTRACT

A source-side radiation detector (SSRD) includes a detector module assembly, and a monitoring lens coupled to the detector module assembly, the detector module assembly and the monitoring lens being positioned proximate to an x-ray source, the monitoring lens including a plurality of slits configured to receive x-rays therethrough from the x-ray source, the detector module assembly being configured detect the x-rays transmitted through the slits and to generate information to track a position of a focal spot of the x-ray source.

17 Claims, 9 Drawing Sheets

SOURCE SIDE MONITORING DEVICE FOR AN IMAGING SYSTEM

BACKGROUND OF THE INVENTION

The subject matter disclosed herein relates generally to imaging systems, and more particularly to a source side focal spot monitoring device for an imaging system.

Some known imaging systems, such as computed tomography (CT) imaging systems, include an x-ray source and a detector assembly that are coupled to a gantry. In operation, the x-ray source emits a fan-shaped x-ray beam or a cone-shaped x-ray beam toward a subject or object positioned on a table. The x-ray beam, after being attenuated by the subject, impinges upon the detector assembly. The intensity of the attenuated x-ray beam received at the detector assembly is typically dependent upon the attenuation of the x-ray beam by the subject. Each detector element of the detector assembly produces a separate electrical signal indicative of the attenuated x-ray beam received. These electrical signals are collectively referred to as x-ray attenuation measurements or x-ray images.

Reference normalization is utilized in CT preprocessing operations to reduce or remove the impact of the x-ray source output fluctuation. For this purpose, the conventional detector assembly includes a set of reference channels (also referred to as reference detectors). The reference channels are typically located slightly outside the reconstruction field of view (FOV) of the detector assembly such that the reference channels receive x-ray photons directly from the x-ray source without interference from the scanned subject. In operation, the reference channels monitor the x-ray source flux and the measured signal is applied to the measured projections. The impact of any variations in the x-ray source output on the measured projections is thereby substantially removed.

However, when the CT imaging system is utilized to image relatively larger subjects or objects, the subjects or objects may potentially block a portion of, or all of, the reference channels during the scan. Thus, when the reference channels are blocked, the reference channels receive attenuated x-rays. As a result, the reference channels may generate an invalid normalization value, which degrades the image quality. More specifically, the incorrect normalization may cause streaks and artifacts to appear in displayed images.

BRIEF DESCRIPTION OF THE INVENTION

In one embodiment, a source-side radiation detector (SSRD) is provided. The SSRD includes a detector module assembly, and a monitoring lens coupled to the detector module assembly, the detector module assembly and the monitoring lens being positioned proximate to an x-ray source, the monitoring lens including a plurality of slits configured to receive x-rays there through from the x-ray source, the detector module assembly being configured detect the x-rays transmitted through the slits and to generate information to track a position of a focal spot of the x-ray source.

In another embodiment, an imaging system is provided. The imaging system includes an x-ray source configured to emit energy toward the object, a source-side radiation detector (SSRD) located on a first side of the object, and an imaging detector located a second opposite side of the object, the SSRD outputting data that is utilized to normalize projection data generated by the imaging detector.

In a further embodiment, a method of correcting imaging data is provided. The method includes receiving information from a source-side radiation detector (SSRD), receiving a projection dataset from an imaging detector, and correcting the projection dataset using the information received from the SSRD.

In a further embodiment, a reference tracking radiation detector is provided. The reference tracking radiation detector includes a detector module assembly, and a monitoring lens coupled to the detector module assembly. The detector module assembly and the monitoring lens are positioned proximate to the post patient imaging detector. The monitoring lens includes a plurality of slits configured to receive x-rays therethrough from the x-ray source. The detector module assembly is configured to detect the x-rays transmitted through the slits and to generate information to track a position of a focal spot of the x-ray source.

DETAILED DESCRIPTION OF THE INVENTION

Figure 1:
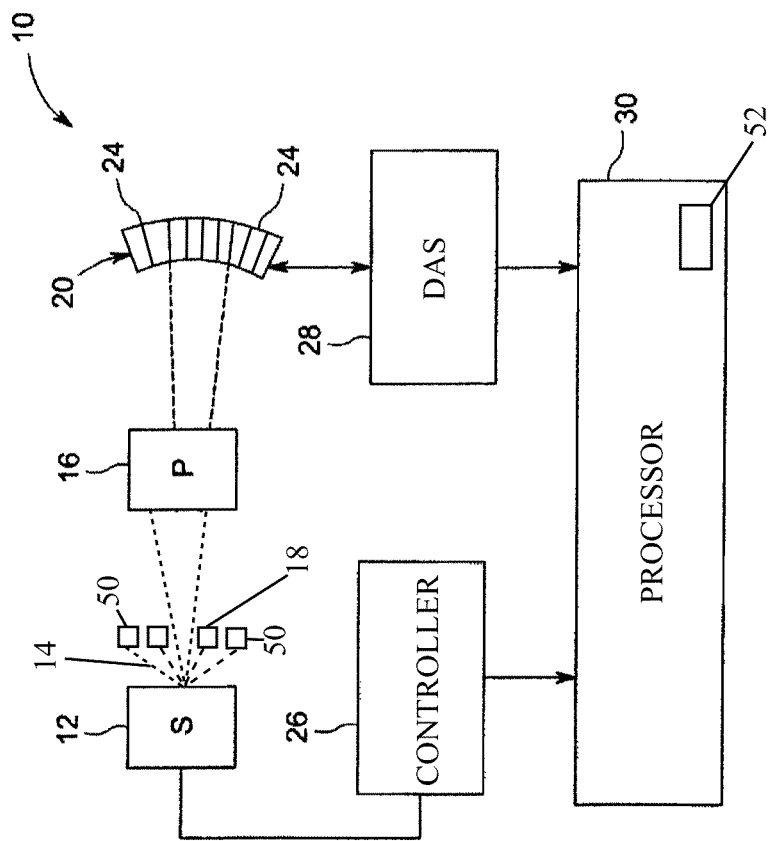
FIG. 1 is a simplified schematic block diagram of an imaging system including a source-side radiation detector (SSRD) formed in accordance with various embodiments.

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

As used herein the term "module" refers to software, hardware, for example, a processor, or a combination thereof that is programmed with instructions for performing an algorithm or method. The modules described herein may communicate wirelessly or through a wired connection.

Various embodiments provide a source-side radiation detector (SSRD) that is located between an x-ray source and a subject being imaged. The SSRD is configured to receive x-rays directly from the x-ray source prior to the x-rays being attenuated by the subject. The information received from the SSRD may be utilized to perform information normalization on information that is acquired from a second imaging detector that is located on an opposite side of the subject being imaged. Accordingly, in various embodiments, the SSRD is located proximate to the x-ray source and functions as a reference sensor to acquire normalization information from the x-ray source and in various embodiments which may be used to correct information acquired from the imaging detector. The SSRD may also track the x-ray source 12, typically the x-ray tube focal spot and intensity of the x-rays emitted from the x-ray source 12.

FIG. 1 is a simplified block diagram of a computed tomography (CT) imaging system 10 that is formed in accordance with various embodiments. The imaging system 10 includes an x-ray source 12 that is configured to emit radiation, e.g., x-rays 14, through a volume containing a subject 16, for example a patient being imaged. In the embodiment shown in FIG. 1, the imaging system 10 also includes an adjustable collimator 18. In operation, the emitted x-rays 14 pass through an opening of the adjustable collimator 18 which limits the angular range associated with the x-rays 14 passing through the volume in one or more dimensions. More specifically, the collimator 18 shapes the emitted x-rays 14, such as to a generally cone or generally fan shaped beam that passes into and through the subject 16. The collimator 18 may be adjusted to accommodate different scan modes, such as to provide a narrow fan-shaped x-ray beam in a helical scan mode and a wider cone-shaped x-ray beam in an axial scan mode. The collimator 18 may be formed, in one embodiment, from two cylindrical disks that rotate to adjust the shape or angular range of the x-rays 14 that pass through the subject 16. Optionally, the collimator 18 may be formed using two or more translating plates or shutters. In various embodiments, the collimator 18 may be formed such that an aperture defined by the collimator 18 corresponds to a shape of an imaging detector 20.

In operation, the x-rays 14 pass through the subject 16 and impinge the imaging detector 20. The imaging detector 20 includes a plurality of detector elements 24 that may be arranged in a single row or a plurality of rows to form an array of detector elements 24. The detector elements 24 generate electrical signals that represent the intensity of the incident x-rays 14. The electrical signals are acquired and processed to reconstruct images of one or more features or structures within the subject 16.

The imaging system 10 also includes an x-ray controller 26 that is configured to provide power and timing signals to the x-ray source 12. The imaging system 10 further includes a data acquisition system 28. In operation, the data acquisition system 28 receives data collected by a readout electronics section of the imaging detector 20. The data acquisition system 28 may receive sampled analog signals from the imaging detector 20 and convert the data to digital signals for subsequent processing by a processor 30. Optionally, the digital-to-analog conversion may be performed by circuitry provided on the imaging detector 20.

The processor 30 is programmed to perform functions described herein, and as used herein, the term processor is not limited to just integrated circuits referred to in the art as computers, but broadly refers to computers, microcontrollers, microcomputers, programmable logic controllers, application specific integrated circuits, and other programmable circuits, and these terms are used interchangeably herein.

The imaging system 10 also includes the SSRD 50 that is located between the x-ray source 12 and the subject 16. In the illustrated embodiment, the SSRD 50 is located adjacent to the collimator 18. However, it should be realized that the SSRD 50 may be located at any position between the x-ray source and the subject 16 and the position shown in FIG. 1 is exemplary only. In operation, the x-rays 14 emitted from the x-ray source 12 impinge on the SSRD 50. Additionally it should be understood that the SSRD 50 may also be located behind the subject 16 as long as SSRD 50 has an unobstructed view of the x-ray source 12. The SSRD 50, as explained in more detail below, includes a plurality of detector elements that are arranged in rows and columns to form an array of detector elements. The SSRD detector elements generate electrical signals that represent the intensity of the incident x-rays 14. The electrical signals are acquired and processed to reconstruct images of one or more features or structures within the subject 16 as is described in more detail below.

In various embodiments, the imaging system 10 also includes a focal spot monitoring module 52 that is configured to receive information from the SSRD 50 and generate information that indicates a position of the focal spot of the x-ray beams 14. In various embodiments, the module 52 is also configured to generate information that indicates an intensity of the focal spot and/or a power level (kVp) of the x-ray beams 14. The module 52 may be configured to automatically determine the focal spot position, the focal spot intensity, and/or the power level of the x-ray beams 14. The module 52 may be implemented as a piece of hardware that is installed in the processor 30. Optionally, the module 52 may be implemented as a set of instructions that are installed on the processor 30. The set of instructions may be stand alone programs, may be incorporated as subroutines in an operating system installed on the processor 30, may be functions in an installed software package on the processor 30, or may be a combination of software and hardware.

Figure 2:
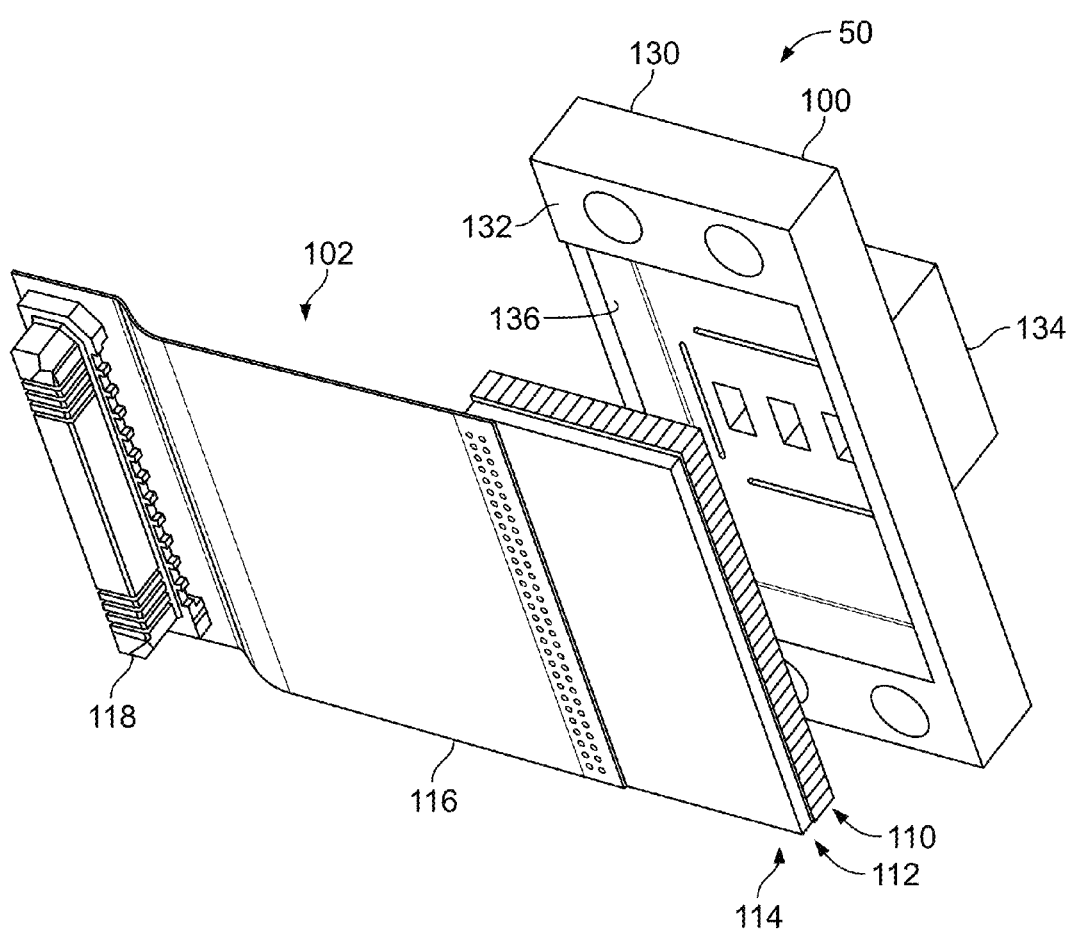
FIG. 2 is a partially exploded view of the SSRD shown in FIG. 1.

FIG. 2 is a partially exploded view of the SSRD 50 shown in FIG. 1. The SSRD 50 includes a monitoring lens 100 and a detector module assembly 102. In various embodiments, the detector module assembly 102 includes a plurality of scintillators 110. The scintillators 110, when struck by an incoming x-ray beam, absorb the energy of the x-ray beam, and re-emit the absorbed energy in the form of light. The detector module assembly 102 further includes a plurality of photosensors or photodiodes 112 for receiving the light energy from an adjacent scintillator and producing electrical signals there from. Typically, each scintillator 110 converts x-rays to light energy. Moreover, each photodiode 112 detects the light energy and generates a corresponding electrical signal as a function of the light emitted by a corresponding scintillator 110. The electrical signals are processed by a readout electronics section 114 and transmitted to the data processor 30 and/or the module 50 for subsequent processing and image reconstruction. In various embodiments, the detector module assembly 102 may be coupled to the processor 30, for example, using a flexible cable 116 and a connector 118.

In various embodiments, the monitoring lens 100 includes a first side 130 and an opposite second side 132. The monitoring lens 100 also includes a portion 134 that extends or projects outwardly from the first side 130. In various embodiments, a plurality of openings, described in more detail below, are formed through the portion 134. The second side 132 has a recess 136 formed therein. The recess 136 is sized to receive the detector module assembly 102 therein. Accordingly, in the illustrated embodiment, the recess 136 has a shape or size that is similar to a shape or size of the detector module assembly 102 to limit the movement of the detector module assembly 102 when installed in the recess 136. In various embodiments, the monitoring lens 100 is fabricated as a single unitary device. More specifically, the monitoring lens 100 may be fabricated as a single piece in a single molding operation or stamped as a single piece. The monitoring lens 100 is fabricated from a material that substantially inhibits x-rays from passing through. For example, the monitoring lens 100 may be fabricated from, for example, a lead material. The monitoring lens 100 may also be fabricated from multiple separate pieces that when combined form the monitoring lens 100. Further, it should be understood that multiple slots or multiple holes may be used for focal spot tracking. The monitoring lens 100 may be constructed, for example, by machining solid blocks of material, casting, metal injection molding and/or a combination of these techniques for multi piece lens designs.

Figure 3:
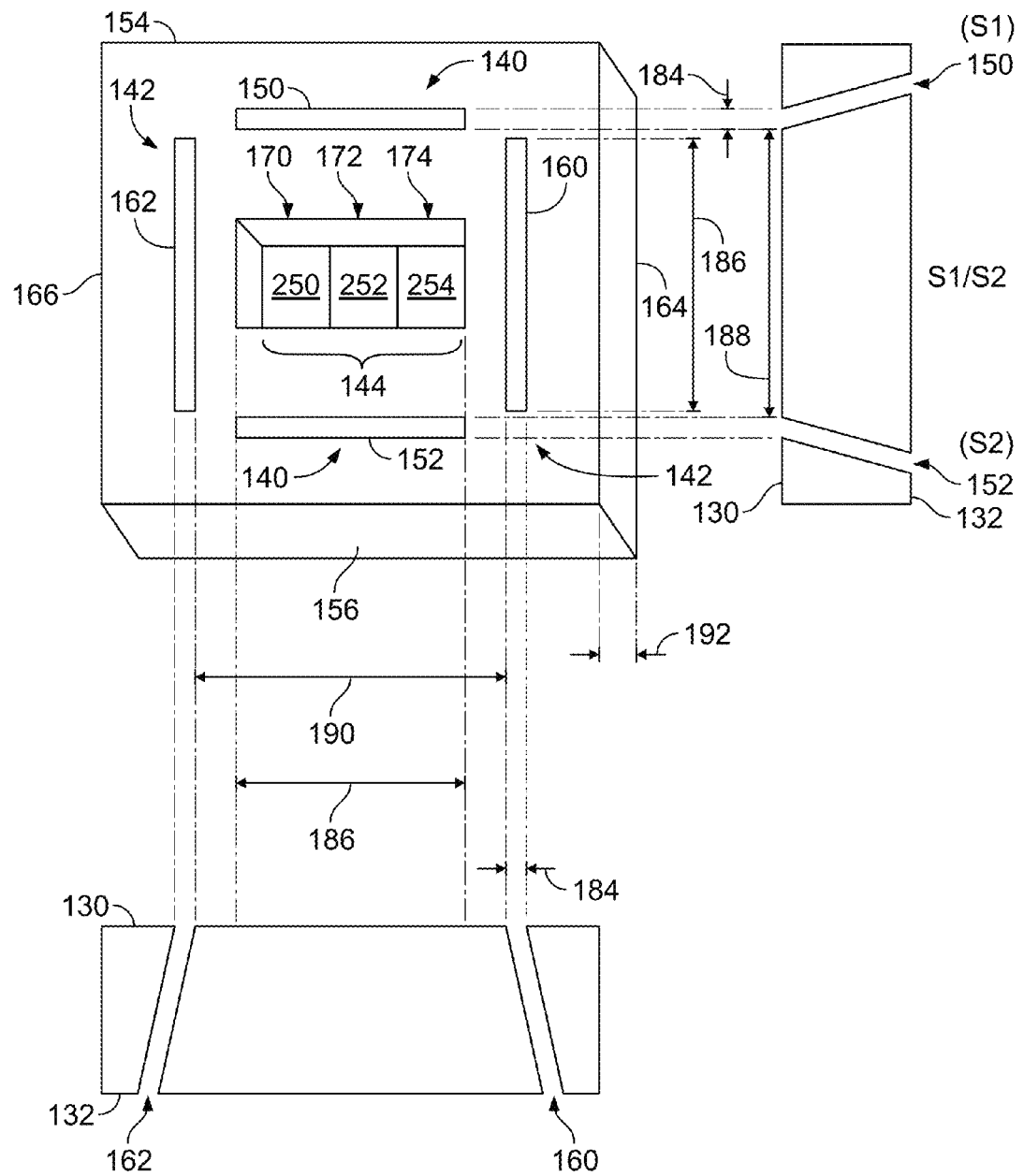
FIG. 3 is a front perspective view of a monitoring lens shown in FIG. 2 formed in accordance with various embodiments.
Figure 4:
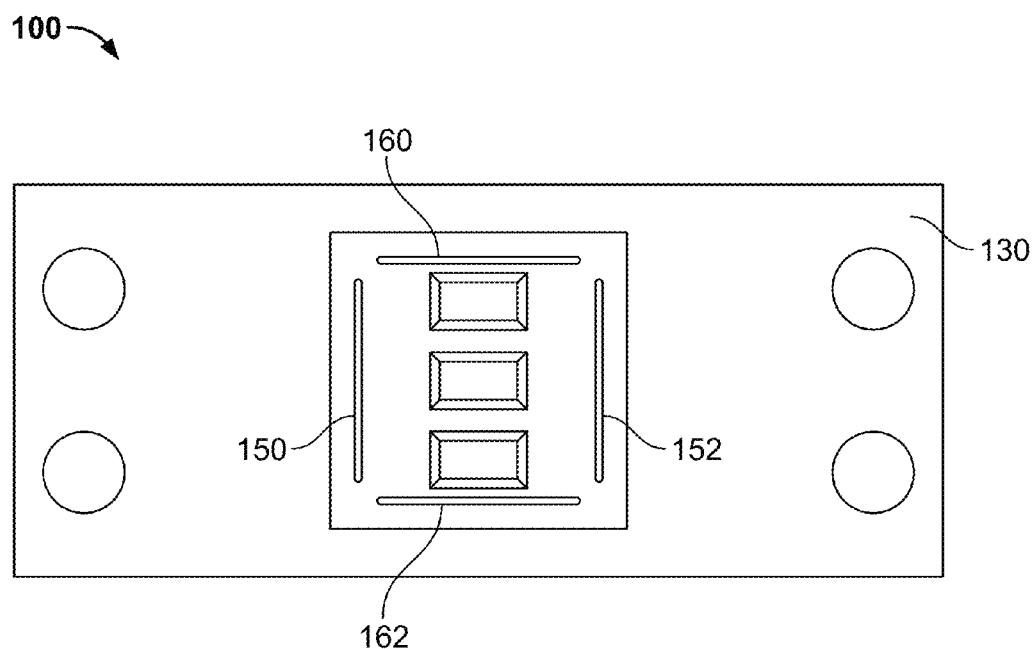
FIG. 4 is a top view of the monitoring lens shown in FIG. 2.
Figure 5:
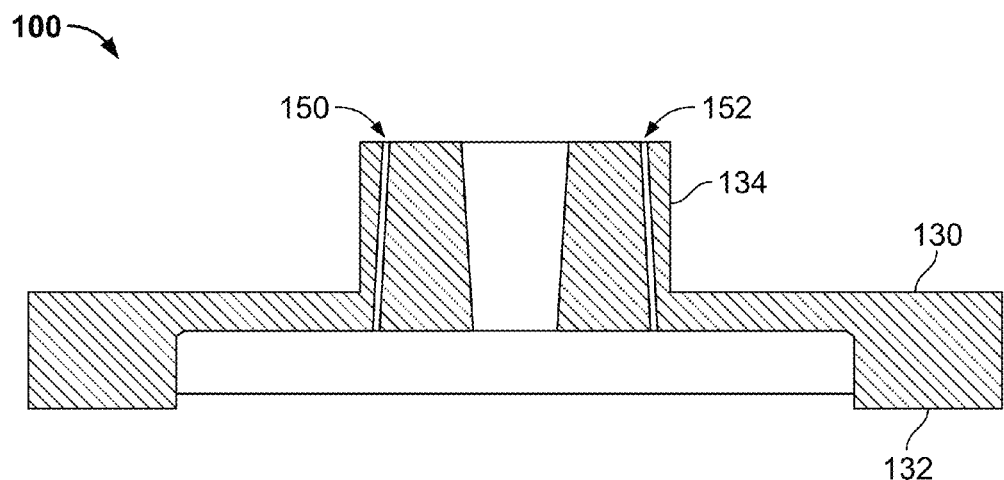
FIG. 5 is a side view of the monitoring lens shown in FIG. 2.
Figure 6:
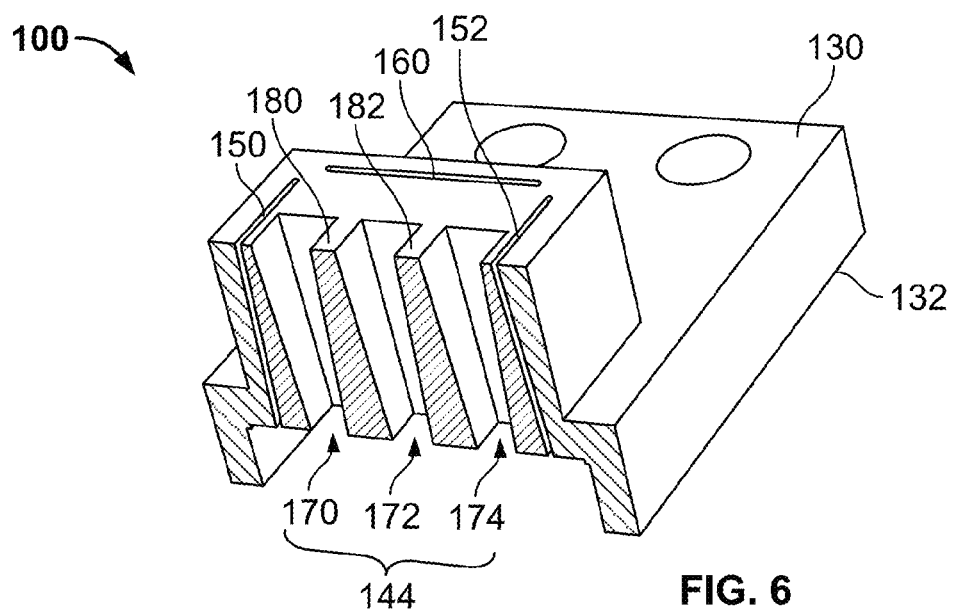
FIG. 6 is a cross-sectional view of a portion of the monitoring lens shown in FIG. 2

FIG. 3 is a front perspective view of the monitoring lens 100 shown in FIG. 2. FIG. 4 is a top view of the monitoring lens 100 shown in FIG. 2. FIG. 5 is a side view of the monitoring lens 100 shown in FIG. 2. FIG. 6 is a cross-sectional view of a portion of the monitoring lens 100 shown in FIG. 2. As shown in FIGS. 3-6, in various embodiments, the monitoring lens 100 includes a plurality of slits and a plurality of openings formed there through. More specifically, the slits and openings enable x-rays impinging on the first side 130 to be transmitted through the monitoring lens 100 to the second side 132 and impinge on the detector module assembly 102. The detector module assembly 102 then detects the x-rays and generates an output as described in more detail below.

In various embodiments, the monitoring lens 100 includes a first pair of slits 140 and a second pair of slits 142. As used herein, a slit is an opening that has a relatively narrow width and a length that is substantially greater than its width, e.g. a rectangle. The monitoring lens 100 also includes at least one opening 144. In the illustrated embodiment, the monitoring lens includes three openings 144. However, it should be realized that the monitoring lens may include a single opening 144, two openings 144, or more than three openings 144. In the illustrated embodiment, the first pair of slits 140 includes a first slit 150 and a second slit 152. Like wise slits 160 and 162 form another slit pair disposed 90 degrees from slit pair 150 and 152. Each slit pair lays on a plane that has opposite angular offsets from a central plane between the slits. The central planes would be the Y-Z plane for the x-slits and the Y-X plane for the Z slits. The angle of the slit pair determines the focus of the slit pair which falls typically before the focal spot. That is, the slit pairs produce converging projects on intersection planes that are at an angle to each other. The aspect ratio of the slit (width to depth) is a design parameter that determines the sensitivity of the lens for tracking the focal spot, wherein the larger the ratio of length to width the more sensitive the tracking capability. Additionally this aspect ratio determines the ability of the slit to reject off axis scatter x-ray, which drives over all signal to noise ratio.

As described above, in addition to the slits 150, 152, 160, and 162, the monitoring lens 100 also includes at least one opening 144. In the illustrated embodiment, the monitoring lens 100 includes a first opening 170, a second opening 172, and a third opening 174. In the illustrated embodiment, the first opening 170 is disposed proximate to the fourth side 166, the third opening 174 is disposed proximate to the third side 164, and the second opening 172 is disposed between the first and third openings 170 and 174, respectively. Moreover, the plurality of openings 144 are disposed inwardly from the first and second pair of slits 140 and 142, respectively. As shown in FIG. 6, the opening 170 is separated from the opening 172 by a divider 180 which is formed integrally as part of the monitoring lens 100. Moreover, the second opening 172 is separated from the third opening 174 by a divider 182 which is also formed integrally with the monitoring lens 100. In operation, the dividers 180 and 182 function as collimators to collimate the x-rays into either the first, second, or third opening 170, 172 or 174, respectively. The operation of the openings 144 is discussed in more detail below.

Referring to FIG. 3, each of the slits 150, 152, 154, and 156 have a width 184 and a length 186. The slit 150 is separated from the slit 152 by a distance 188 and the slit 160 is separated from the slit 162 by a distance 190. In the illustrated embodiment, the length and width of the slits 150 and 152 is substantially the same as the length and width of the slits 160 and 162. However, it should be appreciated that in various other embodiments, the length and width of the slits 150 and 152 may be different than the length and width of the slits 160 and 162. Moreover, the monitoring lens 100 has a thickness 192.

Figure 7:
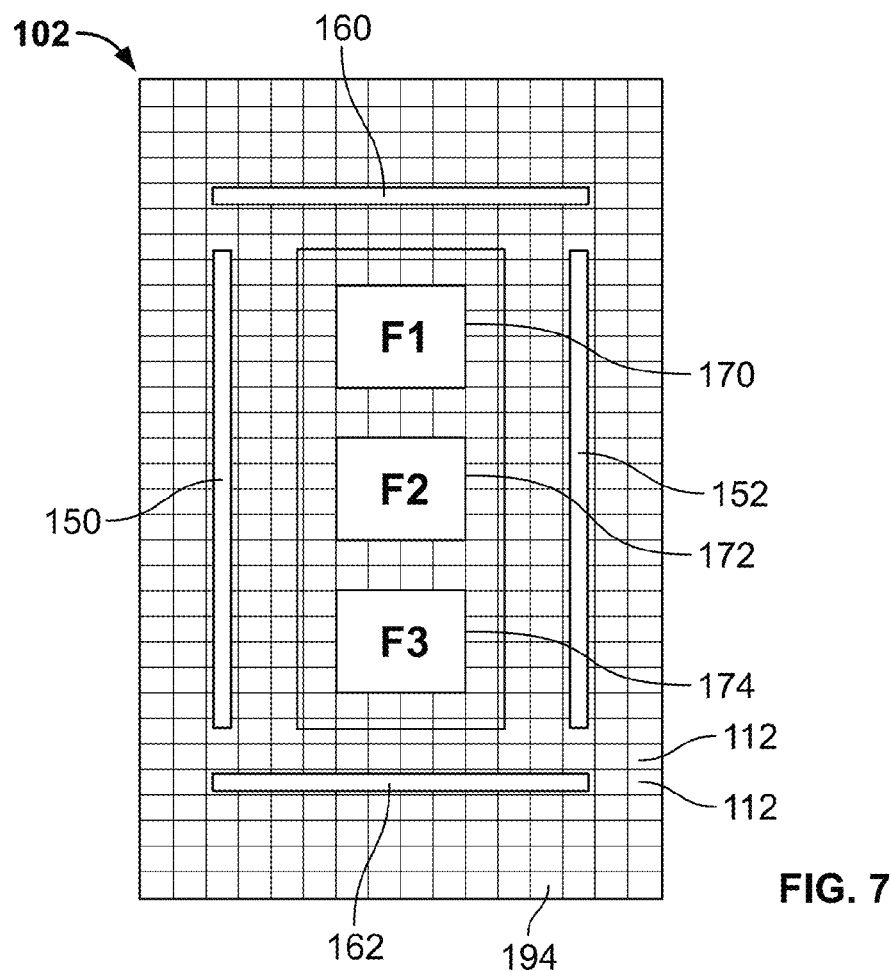
FIG. 7 is a drawing showing the arrangement of a pairs of slits and a plurality of openings with respect to the detector module assembly shown in FIG. 2 in accordance with various embodiments.

FIG. 7 is a simplified diagram showing the arrangement of the first and second pairs of slits 140 and 142, and the plurality of openings 144 with respect to the detector module assembly 102. As described above, the slits 150, 152, 160, and 162 have a relatively narrow width and a length that is substantially greater than its width, e.g. a rectangle. In the illustrated embodiment, each of the slits 150, 152, 160, and 162 has a width that is approximately one pixel wide. Moreover, each of the slits 150, 152, 160, and 162 has a length that extends approximately twelve pixels. Moreover, each of the openings 144 has a width that extends over approximately four pixels and a width that extends over approximately three pixels. Thus, in operation x-rays transmitted through each respective opening 144 are detected by an M×N array of pixels, wherein in the illustrated embodiment, M=3 and N=4. Moreover, each of the x-rays transmitted through the slits 150, 152, 160, and 162 are detected by an O×P array of pixels, wherein in the illustrated embodiment, O=1 and P=12. In the illustrated embodiment, each photosensor 112 defines a pixel 194. Thus, the electrical signal generated by each pixel 194 corresponds to a pixel in the resulting image.

In various embodiments, the SSRD 50 may be utilized to correct or compensate for focal spot motion (which may cause penumbra and gain variation between neighboring channels). More specifically, the SSRD 50 may perform focal spot tracking using the first and second pairs of slits 140 and 142. In operation, the first pair of slits 140 is utilized to track the movement of the x-ray focal spot in a first direction or along a first imaging axis, e.g. an x-axis, and the second pair of slits 142 are utilized to track the movement of the x-ray focal spot in a second different direction or along a second imaging axis, e.g. a z-axis. For example, the first pair of slits 140 may be utilized to track the focal spot position in the z-direction and the second pair of slits 142 may be utilized to track the focal spot position in the z-direction.

A focal spot is the region from which the radiation projects from the x-ray source 12 (shown in FIG. 1). In various embodiments, the x-rays 14 generated by the x-ray source 12 diverge from the focal spot in a conical pattern. In order to produce an image from an axial scan with acceptable resolution, such as to provide clinically relevant image details, it is desirable for the focal spot to be properly aligned in the x-axis and the z-axis. For example, in operation the imaging system 10 may heat up during due to different factors. The heat may cause a thermal expansion of the some of the radiation source structures which may result in a corresponding shift in the focal spot position. To correct for the shift in the focal spot position, the information acquired from the SSRD 50, i.e. the first and second pairs of slits 140 and 142, is utilized to accurately determine the location of the focal spot during the imaging procedure. The information derived from the first and second pairs of slits 140 and 142 may then be used correct the imaging data acquired from the imaging detector 20.

The focal spot of the x-ray source 12 may also change position relative to the detector collimator 18 due to mechanical deflection caused by rotational forces occurring on the x-ray source 12 and/or the detector assembly 20. One potential additional use of the SSRD 50 is to build a transfer function between the focal spot position relative to rotational speed. Such information may then be applied to collected module data to improve image quality.

Figure 8:
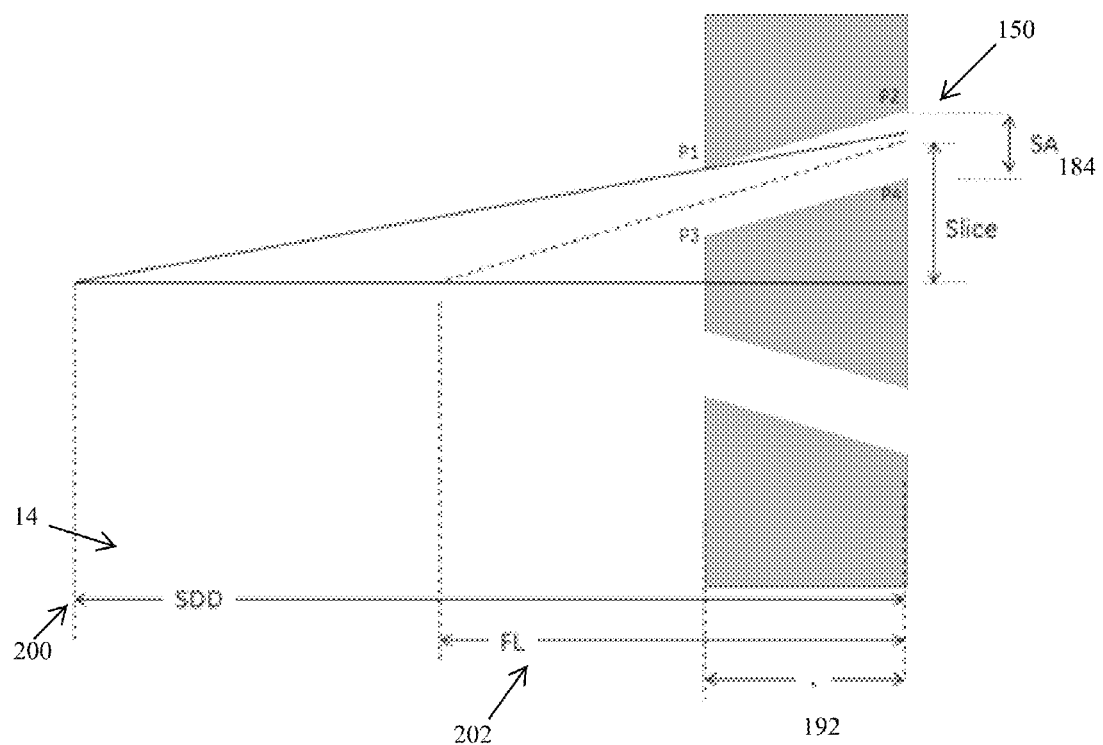
FIG. 8 is a schematic illustration of an exemplary x-ray beam pattern that may be emitted by the x-ray source shown in FIG. 1 in accordance with various embodiments.

FIG. 8 is a schematic illustration of an exemplary x-ray beam pattern that may be emitted by the x-ray source 12 shown in FIG. 1. As shown in FIG. 8, the x-ray beams 14 emanate from a focal spot 200. Moreover, the slit 150 is collimated to a predetermined focal length 202. It should be realized that although only a single slit, i.e. slit 150, is shown, that the operation of the other slits 152, 160, and 162 is similar to the operation of the slit 150. In various embodiments, as the focal spot 200 moves up and down, it should be realized that the signal generated by the slit 150 changes. For example, if the focal spot 200 is in a first position wherein x-rays freely pass through the slit 150, the output from the slit 150, as recorded by the readout electronics section 114 will be at a relatively high level, i.e. the signal will be relatively high because the x-rays are impinging on the pixels 194 located behind the slit 150. Similarly, while the focal spot is 200 is at the first position, the x-rays may not freely pass through the slit 152, thus the output from the slit 152, as recorded by the readout electronics section 114 will be at a relatively lower level than the output from the first slit 150. It should therefore be realized that as a position of the focal spot 200 shifts along the z-axis, for example, the outputs from the first and second slits 150 and 152 will vary. Accordingly, in various embodiments, to determine the focal spot shift in a first axis, such as the z-axis, a ratio $(S_{150}/S_{152})$ of the outputs from the slits 150 and 152 is calculated. The ratio $(S_{150}/S_{152})$ thus represents the focal point movement in along a first axis. In various embodiments, the position of the focal spot along the z-axis, i.e. the ratio $(S_{150}/S_{152})$, may be calculated using for example, the spot position module 52 and/or the processor 30

Similarly, and referring again to FIG. 3, as the focal spot 200 moves side-to-side, it should be realized that the signal generated by the slits 160 and 162 change. For example, if the focal spot 200 is in a first position wherein x-rays freely pass through the slit 160, the output from the slit 160, as recorded by the readout electronics section 114 will be at a relatively high level, i.e. the signal will be relatively high because the x-rays are impinging on the pixels 194 located behind the slit 160. Similarly, while the focal spot is 200 is at the first position, the x-rays may not freely pass through the slit 162, thus the output from the slit 162, as recorded by the readout electronics section 114 will be at a relatively lower level than the output from the first slit 160. It should therefore be realized that as the position of the focal spot 200 shifts along the x-axis, for example, the outputs from the first and second slits 160 and 162 will vary. Accordingly, in various embodiments, to determine the focal spot shift in a second axis, such as the x-axis, a second ratio $(S_{160}/S_{162})$ is calculated and thus represents the focal point movement in along a second axis.

Figure 9:
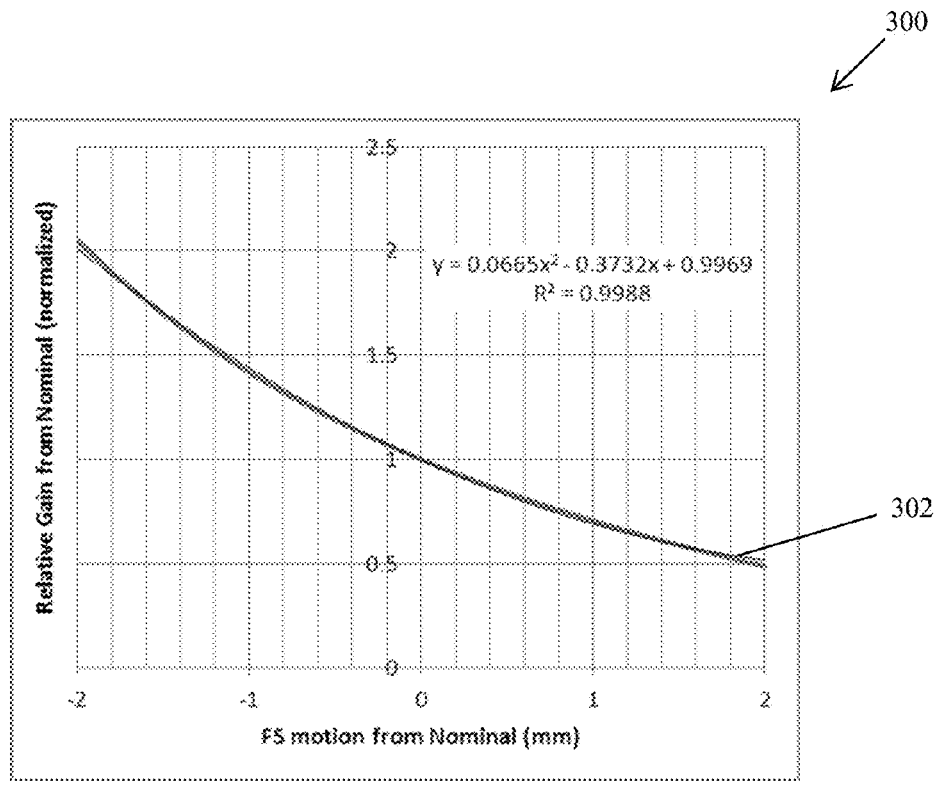
FIG. 9 is a graph illustrating focal spot motion correction values that may be generated in accordance with various embodiments.

FIG. 9 is a graph 300 illustrating focal spot motion correction value 302 that may be generated in accordance with various embodiments wherein the x-axis represents the position of the focal spot 200 and the y-axis represents a gain value that may be applied to the information acquired from the imaging detector 20 to compensate or correct the various views to account for the focal spot movement in the z-direction. In the exemplary embodiment, a line 302 represents the ratio $(S_{150}/S_{152})$ calculated using the slits 150 and 152. Accordingly, as shown in FIG. 9 as the ratio $(S_{150}/S_{152})$ changes, the gain applied to each view in the z-direction also changes accordingly.

Figure 10:
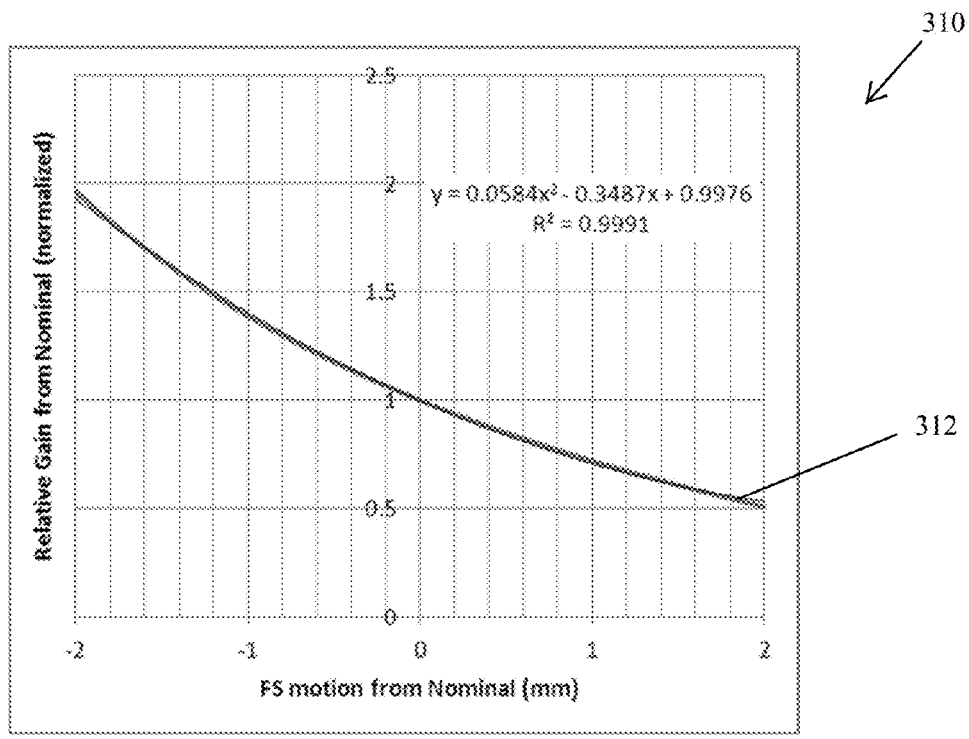
FIG. 10 is a graph illustrating other focal spot motion correction values that may be generated in accordance with various other embodiments.

Similarly, FIG. 10 is a graph 310 illustrating focal spot motion correction value 312 that may be generated in accordance with various embodiments wherein the x-axis represents the position of the focal spot 200 and the y-axis represents a gain value that may be applied to the information acquired from the imaging detector 20 to compensate or correct the various views to account for the focal spot movement in the x-direction. In the exemplary embodiment, a line 312 represents the ratio $(S_{160}/S_{162})$ calculated using the slits 160 and 162. Accordingly, as shown in FIG. 10 as the ratio $(S_{160}/S_{162})$ changes, the gain applied to each view in the x-direction also changes accordingly. It should be realized that in various embodiments, if the focal spot 200 is not moving in the x-direction, but the focal spot 200 is moving in the z-direction, the ratio S3/S4 may be utilized to correct the image data. Similarly, if the focal spot 200 is not moving in the z-direction, but the focal spot 200 is moving in the x-direction, the ratio S1/S2 may be utilized to correct the image data.

Referring again to FIG. 3, as discussed above, the monitoring lens 100 may also include a single opening 144, two openings 144, or more than three openings 144. In the illustrated embodiment, the monitoring lens 100 includes three openings 144. In operation, the openings 144 are utilized to determine both an intensity value of the x-ray beams 14 and/or a power level (kVp) of the x-ray source 12. More specifically, the openings 144 enable the imaging system 10 to track the intensity value of the x-ray beams 14 and/or a power level (kVp) of the x-ray source 12 over time. In various embodiments, each of the openings includes a filter installed therein. For example, the first opening 170 has a filter 250 installed therein, the second opening 172 has a filter 252 installed therein, and the third opening 174 has a filter 254 installed therein. In various embodiments, the filters 250, 252, and 254 are utilized to generate a correction value which is utilized to normalize the projection data acquired from the imaging detector 20. More specifically, to maintain image quality regardless of x-ray intensity, the projection data acquired from the imaging detector 20 is normalized before generating an image. Particularly, and for each view, the projection data is normalized relative to the intensity of the x-rays impinging upon the imaging detector 20. Accordingly, in various embodiments, the filtered information acquired from the filters 250, 252, and 254 is utilized to normalize the projection data acquired from the imaging detector 20. In various embodiments, the filter 250, 252, and 254 are the same filters. For example, the filters 250, 252, and 254 may be implemented as k-edge filters. Accordingly, the filters 250, 252, and 254 absorb the x-rays in a similar manner because they all are embodied as the same k-edge filter. Therefore, the x-ray intensity observed at each of the filters 250, 252, and 254 should be substantially the same. As a result, the outputs from the three filters 250, 252, and 254 may be averaged together to generate the correction value that is used to correct or normalize each view or projection acquired by the imaging detector 20. It is important to note that the shape of the openings used for reference normalization or for kVp measurements are constructed such that their readings are not effected by the focal spot motion or position. To enable this, the side walls of the openings are tapered the opposite of the X and Z tracking slits such that the planes formed parallel to the opening walls converge after the SSRD 50 (following x-ray path).

In various other embodiments, the filter 250 is different than the filter 252. Moreover, the filter 254 is different than the filter 250 and the filter 252. For example, in various embodiments, the filters 250, 252, and 254 may all be implemented as k-edge filters. However, the filter 250 may be fabricated from materials that absorb x-rays at a different rate as a function of kV than the filter 252. Moreover, the filter 254 may absorb x-rays at a different rate as a function of kV than the filters 250 and 252. Accordingly, calculating a ratio of two of the filters generates a value that represents the kV level of the x-ray source 12. For example, a ratio 250/252 may represent the kV level of the x-ray source. Moreover, a ratio 252/254 may represent a kV level of the x-ray source 12. Thus, the filters 250, 252, and 254 provide information which may also be utilized to normalize the projection data acquired by the imaging detector 20.

Figure 11:
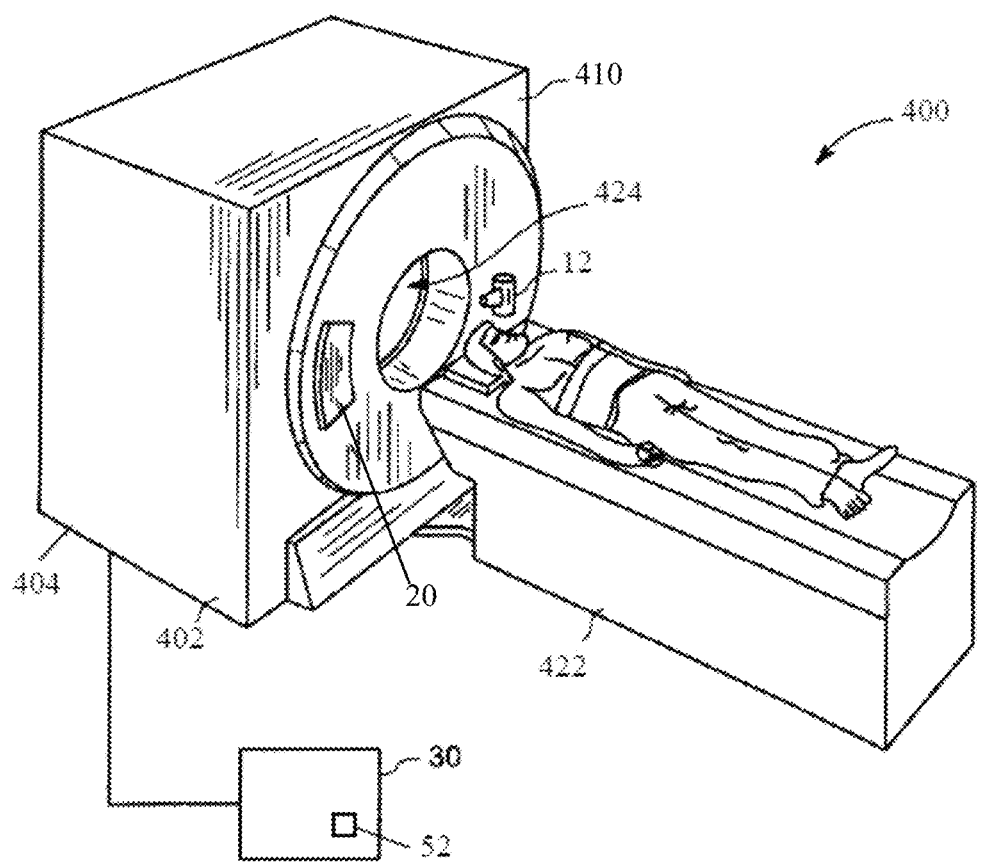
FIG. 11 is a pictorial view of a multi-modality imaging system formed in accordance with various embodiments.
Figure 12:
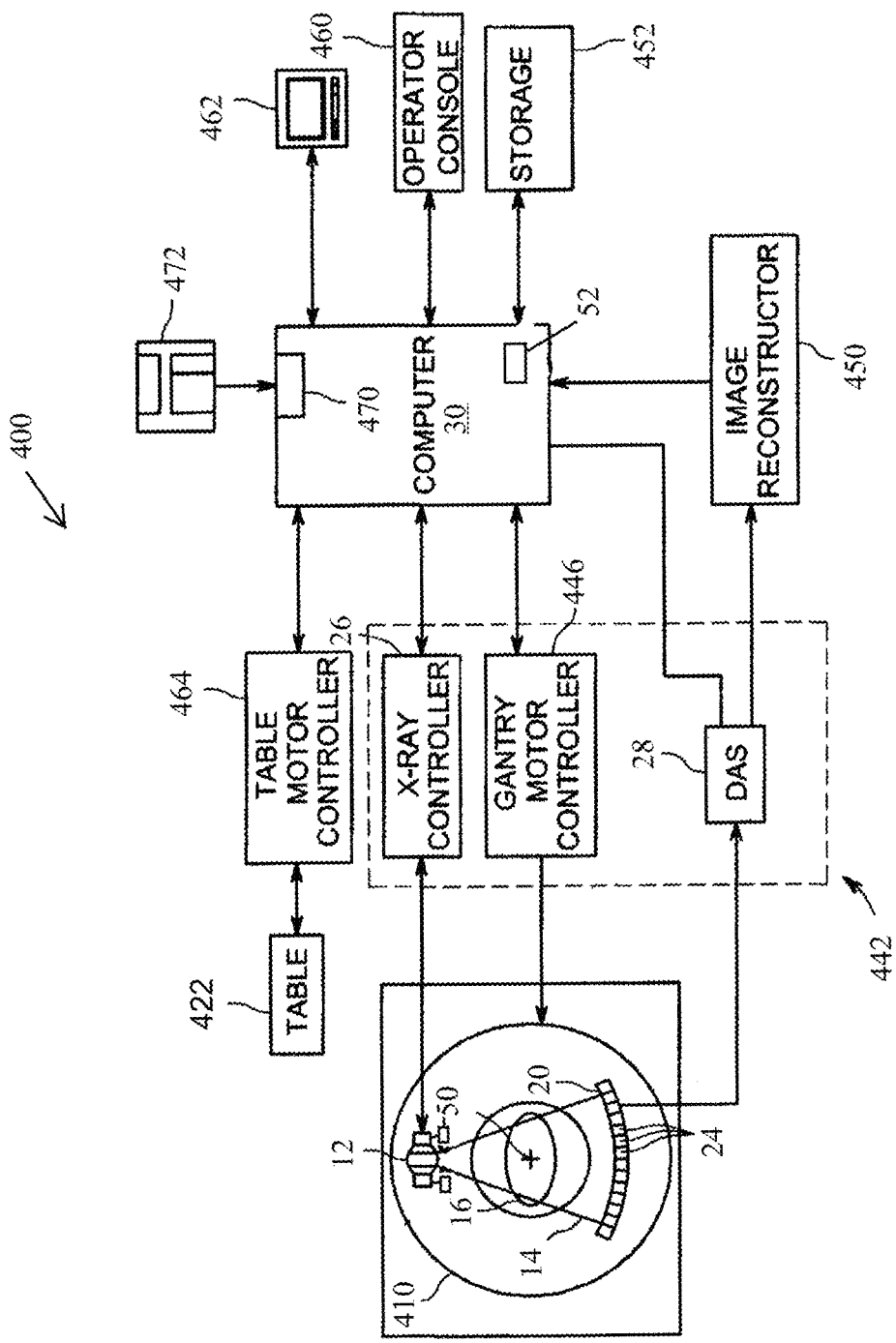
FIG. 12 is a block schematic diagram of the system illustrated in FIG. 8.

FIG. 11 is a perspective view of an exemplary imaging system 400 that may be configured to implement the various embodiments described herein. FIG. 12 is a schematic block diagram of the imaging system 400 (shown in FIG. 11). Although various embodiments are described in the context of an exemplary dual modality imaging system that includes a CT imaging system and a positron emission tomography (PET) imaging system, it should be understood that other imaging systems capable of performing the functions described herein are contemplated as being used.

The multi-modality imaging system 400 is illustrated, and includes a CT imaging system 402 and a PET imaging system 404. The imaging system 400 allows for multiple scans in different modalities to facilitate an increased diagnostic capability over single modality systems. In one embodiment, the exemplary multi-modality imaging system 400 is a CT/PET imaging system 400. Optionally, modalities other than CT and PET are employed with the imaging system 400. For example, the imaging system 400 may be a standalone CT imaging system, a standalone PET imaging system, a magnetic resonance imaging (MRI) system, an ultrasound imaging system, an x-ray imaging system, and/or a single photon emission computed tomography (SPECT) imaging system, interventional C-Arm tomography, CT systems for a dedicated purpose such as extremity or breast scanning, and combinations thereof, among others.

The CT imaging system 402 includes a gantry 410 that has the x-ray source 12 that projects the beam of x-rays 14 toward the imaging detector 20 on the opposite side of the gantry 410. Moreover, the x-ray source 12 also projects the beam of x-rays 14 toward the SSRD 50 that is mounted between the x-ray source and the subject 16. The imaging detector 20 includes the plurality of detector elements 24 that are arranged in rows and channels that together sense the projected x-rays that pass through an object, such as the subject 16. The imaging system 400 also includes the processor 30 that receives the projection data from the imaging detector 20 and processes the projection data to reconstruct an image of the subject 16. Moreover, the processor 30 receives the data from the SSRD 50 and processes the data to correct the imaging data acquired from the imaging detector 20 as described above.

In operation, operator supplied commands and parameters are used by the processor 30 to provide control signals and information to reposition a motorized table 422. More specifically, the motorized table 422 is utilized to move the subject 16 into and out of the gantry 410. Particularly, the table 422 moves at least a portion of the subject 16 through a gantry opening 424 that extends through the gantry 410.

The imaging system 400 also includes the focal spot monitoring module 52 that is configured to implement various methods described herein. For example, the module 52 may be configured automatically determine a position of the focal spot of the x-ray source 12, determine an intensity of the focal spot, and also determine a power of the x-rays from the x-ray source 12. The information determined by the focal spot monitoring module 52 may be applied to the transmission data acquired from the imaging detector 20 to perform various projection data corrections as described above.

The module 52 may be implemented as a piece of hardware that is installed in the processor 30. Optionally, the module 52 may be implemented as a set of instructions that are installed on the processor 30. The set of instructions may be stand alone programs, may be incorporated as subroutines in an operating system installed on the processor 30, may be functions in an installed software package on the processor 30, and the like. It should be understood that the various embodiments are not limited to the arrangements and instrumentality shown in the drawings.

As discussed above, the detector 20 includes a plurality of detector elements 24. Each detector element 24 produces an electrical signal, or output, that represents the intensity of an impinging x-ray beam and hence allows estimation of the attenuation of the beam as it passes through the subject 16. During a scan to acquire the x-ray projection data, the gantry 410 and the components mounted thereon rotate about a center of rotation 440. FIG. 12 shows only a single row of detector elements 24 (i.e., a detector row). However, the multislice detector array 20 includes a plurality of parallel detector rows of detector elements 24 such that projection data corresponding to a plurality of slices can be acquired simultaneously during a scan.

Rotation of the gantry 410 and the operation of the x-ray source 12 are governed by a control mechanism 442. The control mechanism 442 includes the x-ray controller 26 that provides power and timing signals to the x-ray source 12 and a gantry motor controller 446 that controls the rotational speed and position of the gantry 410. The data acquisition system (DAS) 28 in the control mechanism 442 samples analog data from detector elements 24, and the SSRD 50, and converts the data to digital signals for subsequent processing. For example, the subsequent processing may include utilizing the module 52 to implement the various methods described herein. An image reconstructor 450 receives the sampled and digitized x-ray data from the DAS 28 and performs high-speed image reconstruction. The reconstructed images are input to the processor 30 that stores the image in a storage device 452. Optionally, the processor 30 may receive the sampled and digitized x-ray data from the DAS 28 and perform various methods described herein using the module 52. The processor 30 also receives commands and scanning parameters from an operator via a console 460 that has a keyboard. An associated visual display unit 462 allows the operator to observe the reconstructed image and other data from computer.

The operator supplied commands and parameters are used by the processor 30 to provide control signals and information to the DAS 28, the x-ray controller 26 and the gantry motor controller 446. In addition, the processor 30 operates a table motor controller 464 that controls the motorized table 422 to position the subject 406 in the gantry 410. Particularly, the table 422 moves at least a portion of the subject 16 through the gantry opening 424 as shown in FIG. 11.

Referring again to FIG. 12, in one embodiment, the processor 30 includes a device 470, for example, a CD-ROM drive, a DVD drive, a magnetic optical disk (MOD) device, or any other digital device including a network connecting device such as an Ethernet device for reading instructions and/or data from a non-transitory computer-readable medium 472, such as a CD-ROM, a DVD or another digital source such as a network or the Internet. In another embodiment, the processor 30 executes instructions stored in firmware (not shown). The processor 30 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 12, the imaging detector 20, and the SSRD 50 are rotated with the gantry 410 within the imaging plane and around the subject 16 to be imaged such that the angle at which an x-ray beam 474 intersects the subject 16 constantly changes. A group of x-ray attenuation measurements, i.e., projection data, from the imaging detector 20 at one gantry angle is referred to as a "view". A "scan" of the subject 16 comprises a set of views made at different gantry angles, or view angles, during one revolution of the x-ray source 12, the imaging detector 20, and the SSRD 50. In a CT scan, the projection data is processed to reconstruct an image that corresponds to a two dimensional slice taken through the subject 16.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A source-side radiation detector (SSRD) comprising:
   a detector module assembly; and
   a monitoring lens coupled to the detector module assembly, the detector module assembly and the monitoring lens being positioned proximate to an x-ray source, the monitoring lens including a plurality of slits configured to receive x-rays therethrough from the x-ray source, the detector module assembly being configured to detect the x-rays transmitted through the slits and to generate information to track a position of a focal spot of the x-ray source, wherein the plurality of slits comprises a first pair of slits arranged in a first direction and a second pair of slits arranged in a different second direction.

2. The SSRD of claim 1, wherein
   the first pair of slits generate information that indicates a motion of the focal spot in a first direction, the first pair of slits being arranged perpendicular to the second pair of slits, wherein the second pair of slits generate information that indicates a motion of the focal spot in a second direction.

3. The SSRD of claim 1, wherein the monitoring lens further comprises at least one opening disposed between the plurality of slits, the opening configured to receive x-rays therethrough from the x-ray source, the detector module assembly being configured to detect the x-rays transmitted through the opening and to generate information that indicates an intensity of the focal spot.

4. The SSRD of claim 1, wherein the monitoring lens further comprises three openings, each of the three openings having a different filter installed therein, the three openings configured to receive x-rays therethrough from the x-ray source, the detector module assembly being configured to compare an output from a first opening to an output from a second opening to generate information that indicates a power of the x-rays.

5. The SSRD of claim 1, wherein the focal spot information is used to normalize data acquired from an imaging detector that is located on an opposite side of an object as the monitoring lens.

6. A source-side radiation detector (SSRD) comprising:
a detector module assembly; and
a monitoring lens coupled to the detector module assembly, the detector module assembly and the monitoring lens being positioned proximate to an x-ray source, the monitoring lens including a plurality of slits configured to receive x-rays therethrough from the x-ray source, the detector module assembly being configured to detect the x-rays transmitted through the slits and to generate information to track a position of a focal spot of the x-ray source, wherein the monitoring lens further comprises a plurality of openings, each of the openings having a filter installed therein, the plurality of openings configured to receive x-rays therethrough from the x-ray source, the detector module assembly being configured to detect the x-rays transmitted through the plurality of openings and to generate information that indicates an intensity of the focal spot.

7. A source-side radiation detector (SSRD) comprising:
a detector module assembly; and
a monitoring lens coupled to the detector module assembly, the detector module assembly and the monitoring lens being positioned proximate to an x-ray source, the monitoring lens including a plurality of slits configured to receive x-rays therethrough from the x-ray source, the detector module assembly being configured to detect the x-rays transmitted through the slits and to generate information to track a position of a focal spot of the x-ray source, wherein the monitoring lens further comprises a plurality of openings, each of the openings having a different filter installed therein, the plurality of openings configured to receive x-rays therethrough from the x-ray source, the detector module assembly being configured to detect the x-rays transmitted through the plurality of openings and to generate information that indicates an power of the x-rays.

8. An imaging system for imaging an object, the imaging system comprising:
an x-ray source configured to emit energy toward the object;
a source-side radiation detector (SSRD) located on a first side of the object; and
an imaging detector located on a second opposite side of the object, the SSRD outputting data that is utilized to normalize projection data generated by the imaging detector, wherein the SSRD comprises:
a detector module assembly; and
a monitoring lens coupled to the detector module assembly, the monitoring lens including a plurality of slits configured to receive x-rays therethrough from the x-ray source, the detector module assembly being configured to detect the x-rays transmitted through the slits and to generate information to track a position of a focal spot of the x-ray source, wherein the plurality of slits comprises a first pair of slits arranged in a first direction and a second pair of slits arranged in a different second direction.

9. The imaging system of claim 8, wherein
the first pair of slits generate information that indicates a motion of the focal spot in a first direction,
the first pair of slits being arranged perpendicular to the second pair of slits, wherein the second pair of slits generate information that indicates a motion of the focal spot in a second direction.

10. The imaging system of claim 8, wherein the monitoring lens further comprises at least one opening disposed between the plurality of slits, the opening configured to receive x-rays therethrough from the x-ray source, the detector module assembly being configured to detect the x-rays transmitted through the opening and to generate information that indicates an intensity of the focal spot.

11. The imaging system of claim 8, wherein the monitoring lens further comprises three openings, each of the three openings having a different filter installed therein, the three openings configured to receive x-rays therethrough from the x-ray source, the detector module assembly being configured to compare an output from a first opening to an output from a second opening to generate information that indicates a power of the x-rays.

12. An imaging system for imaging an object, the imaging system comprising:
an x-ray source configured to emit energy toward the object;
a source-side radiation detector (SSRD) located on a first side of the object; and
an imaging detector located on a second opposite side of the object, the SSRD outputting data that is utilized to normalize projection data generated by the imaging detector, wherein the SSRD comprises: a detector module assembly; and a monitoring lens coupled to the detector module assembly, the monitoring lens including a plurality of slits configured to receive x-rays therethrough from the x-ray source, the detector module assembly being configured to detect the x-rays transmitted through the slits and to generate information to track a position of a focal spot of the x-ray source, wherein the monitoring lens further comprises a plurality of openings, each of the openings having a filter installed therein, the plurality of openings configured to receive x-rays therethrough from the x-ray source, the detector module assembly being configured to detect the x-rays transmitted through the plurality of openings and to generate information that indicates an intensity of the focal spot.

13. An imaging system for imaging an object, the imaging system comprising:
an x-ray source configured to emit energy toward the object;
a source-side radiation detector (SSRD) located on a first side of the object; and an imaging detector located on a second opposite side of the object, the SSRD outputting data that is utilized to normalize projection data generated by the imaging detector, wherein the SSRD comprises: a detector module assembly; and a monitoring lens coupled to the detector module assembly, the monitoring lens including a plurality of slits configured to receive x-rays therethrough from the x-ray source, the detector module assembly being configured to detect the x-rays transmitted through the slits and to generate information to track a position of a focal spot of the x-ray source, wherein the monitoring lens further comprises a plurality of openings, each of the openings having a different filter installed therein, the plurality of openings configured to receive x-rays therethrough from the x-ray source, the detector module assembly being configured to detect the x-rays transmitted through the plurality of openings and to generate information that indicates an power of the x-rays.

14. A method for correcting imaging data, said method comprising:
   receiving information from a source-side radiation detector (SSRD) that is disposed on a first side of an object being imaged;
   receiving a projection dataset from an imaging detector that is located on an opposite second side of the object being imaged; and
   correcting the projection dataset using the information received from the SSRD, wherein the SSRD comprises a first pair of slits arranged in a first direction and a second pair of slits arranged in a different second direction, said method further comprising:
      generating information that indicates a motion of the focal spot in a first direction using the first pair of slits;
      generating information that indicates a motion of the focal spot in a second direction using the second pair of slits; and
      correcting the projection dataset using the information that indicates the focal spot motion in the first and second directions.

15. The method of claim 14, wherein the SSRD further comprises at least one opening disposed between the first and second pairs of slits, said method comprising generating information that indicates an intensity of the focal spot using the at least one opening.

16. The method of claim 14, wherein the SSRD comprises a plurality of openings, each of the openings having a different filter installed therein, said method further comprising generating information that indicates a power of the x-ray source using information acquired from the plurality of filtered openings.

17. A reference tracking radiation detector comprising:
   a detector module assembly; and
   a monitoring lens coupled to the detector module assembly, the detector module assembly and the monitoring lens being positioned proximate to a post patient imaging detector, the monitoring lens including a plurality of slits configured to receive x-rays therethrough from an x-ray source, the detector module assembly being configured to detect the x-rays transmitted through the slits and to generate information to track a position of a focal spot of the x-ray source, wherein the plurality of slits comprises a first pair of slits arranged in a first direction and a second pair of slits arranged in a different second direction.

* * * * *